United States Patent [19]
Campero et al.

[11] Patent Number: 5,873,844
[45] Date of Patent: Feb. 23, 1999

[54] METHOD AND APPARATUS FOR NUMBING TISSUE BEFORE INSERTING A NEEDLE

[76] Inventors: Manuel Campero, 1229 7th St., Wafco, Calif. 93280; Jerry Roane, 101 Laurelwood Dr. South, Austin, Tex. 78733

[21] Appl. No.: 787,580

[22] Filed: Jan. 22, 1997

[51] Int. Cl.⁶ .................................................. H61B 17/22
[52] U.S. Cl. ................................................ 601/2; 433/119
[58] Field of Search ................................. 601/2; 604/22; 600/439, 437; 433/86, 119

[56] References Cited

U.S. PATENT DOCUMENTS

| | | | |
|---|---|---|---|
| 4,870,953 | 10/1989 | DonMichael et al. | 601/2 |
| 4,920,954 | 5/1990 | Alliger et al. | 601/2 |
| 4,940,468 | 7/1990 | Petillo | 606/170 |
| 5,269,297 | 12/1993 | Weng et al. | 601/2 |
| 5,368,557 | 11/1994 | Nita et al. | 601/2 |
| 5,423,838 | 6/1995 | Willard | 600/439 |
| 5,427,118 | 6/1995 | Nita et al. | 601/2 |
| 5,437,606 | 8/1995 | Tsukamoto | 601/2 |
| 5,449,369 | 9/1995 | Imran | 606/159 |
| 5,498,236 | 3/1996 | Dubrul et al. | 601/2 |
| 5,639,238 | 6/1997 | Fishburne, Jr. | 433/215 |
| 5,647,851 | 7/1997 | Pokras | 604/131 |

*Primary Examiner*—Brian Casler

[57] ABSTRACT

A method and apparatus for numbing tissue before a shot is inserted into the tissue wherein said method and apparatus provide a vibratory force the tissue, thereby overexciting the nerves in the tissue and blocking the nerves' ability to sense pain.

2 Claims, 4 Drawing Sheets

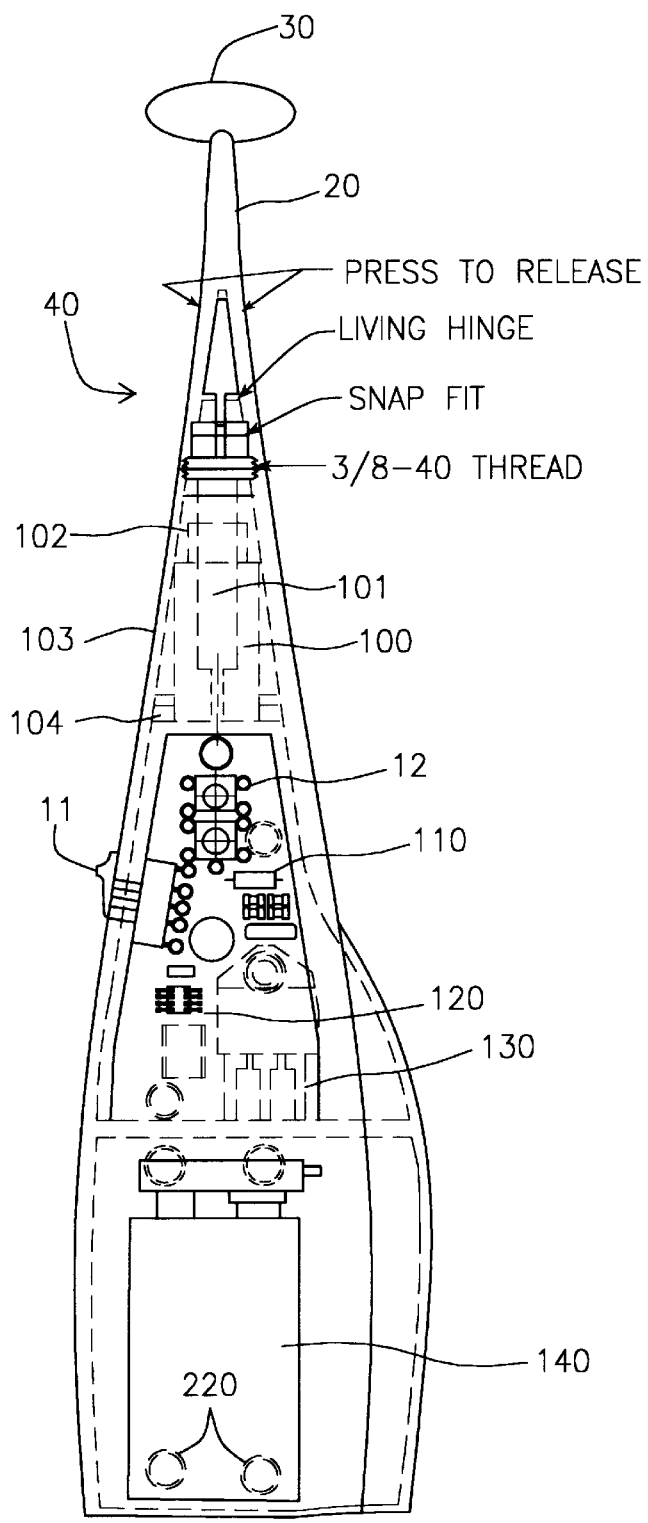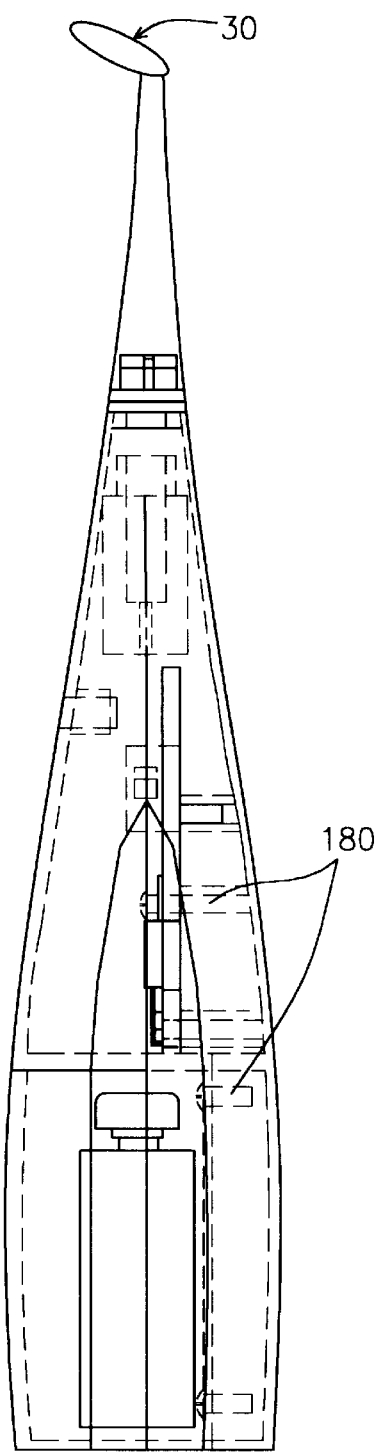
FIG. 2
FIG. 3

METHOD AND APPARATUS FOR NUMBING TISSUE BEFORE INSERTING A NEEDLE

BACKGROUND OF THE INVENTION

1. Field of The Invention

Applicant's invention relates to a method or apparatus for eliminating the pain associated with receiving medical shots, particularly in dental procedures.

2. Background Information

Dental procedures often inflict a great degree of pain upon patients. To reduce this pain, dentists frequently use local anesthesia which is injected into the gums of patients by a syringe and needle before the commencement of painful dental procedures. The anesthesia deadens the nerves and allows the dentist to operate without creating excessive pain and discomfort for the patient. However, often dentists must administer a large quantity of anesthesia in a number of shots, causing many patients to wonder whether the pain for the shots exceeds the pain of the dental procedure. To lessen the pain inflicted upon patients when shots are administered, dentists will sometimes rub oral anesthetic ointment on the patient's gums or shake the patients' lip before administering the shots.

Other methods exist for deadening pain in dental operations, either with anesthesia or without anesthesia. For instance, U.S. Pat. No. 5,437,606 by Tsukamoto discloses a device that uses ultrasonic vibration to increase the rate at which anesthesia becomes effective by improving the infusion and diffusion of anesthesia into the gums of a patient. Other devices, such as are disclosed in U.S. Pat. No. 4,608,019 by Kumabe et al., and U.S. Pat. No. 4,496,321 by Kumabe et al., include cutting devices which vibrate the patient's tooth at a rate which deadens the nerves of the tooth. However, none of these devices present a means of reducing or eliminating the pain associated with the initial application of anesthesia by needle to a patient.

SUMMARY OF THE INVENTION

The present invention presents a method and apparatus for deadening pain associated with the application of injected anesthesia to a patient. The present invention provides a vibratory force to a patient's tissue which stimulates the nerve connections in the tissue. This stimulation causes the nerve connections to send multiple signals to the patient's brain, thereby over-riding the brain's capacity to detect and analyze the pain caused when a needle is inserted into the tissue. In effect, the present invention avoids the sensing of painful impulses by over-exciting the tissue with non-painful impulses. The claimed invention is particularly effective in nerve-rich areas of the mouth and gums, but can also be used on tissue in other parts of the body.

BRIEF DESCRIPTION OF THE DRAWINGS

Applicant's invention may be further understood from a description of the accompanying drawings wherein, unless otherwise specified, like reference numbers are intended to depict like components in the various views.

FIG. 2 is a perspective side view of the preferred embodiment.

FIG. 3 is a perspective front view of the preferred embodiment.

DETAILED DESCRIPTION OF THE PREFERRED EMBODIMENT

The present invention is a method and apparatus for reducing and even eliminating the discomfort associated with receiving shots. By over-exciting nerve tissue with non-painful stimuli, the present invention overrides the brain's ability to detect other sensations, such as the pain normally experienced when shots are injected into the tissue. The method is accomplished by applying a vibratory force to the tissue, such as a rubbing or tapping motion. The preferred embodiment creates the vibratory force with vibratory apparatus as is described in greater detail herein.

Figure 1:
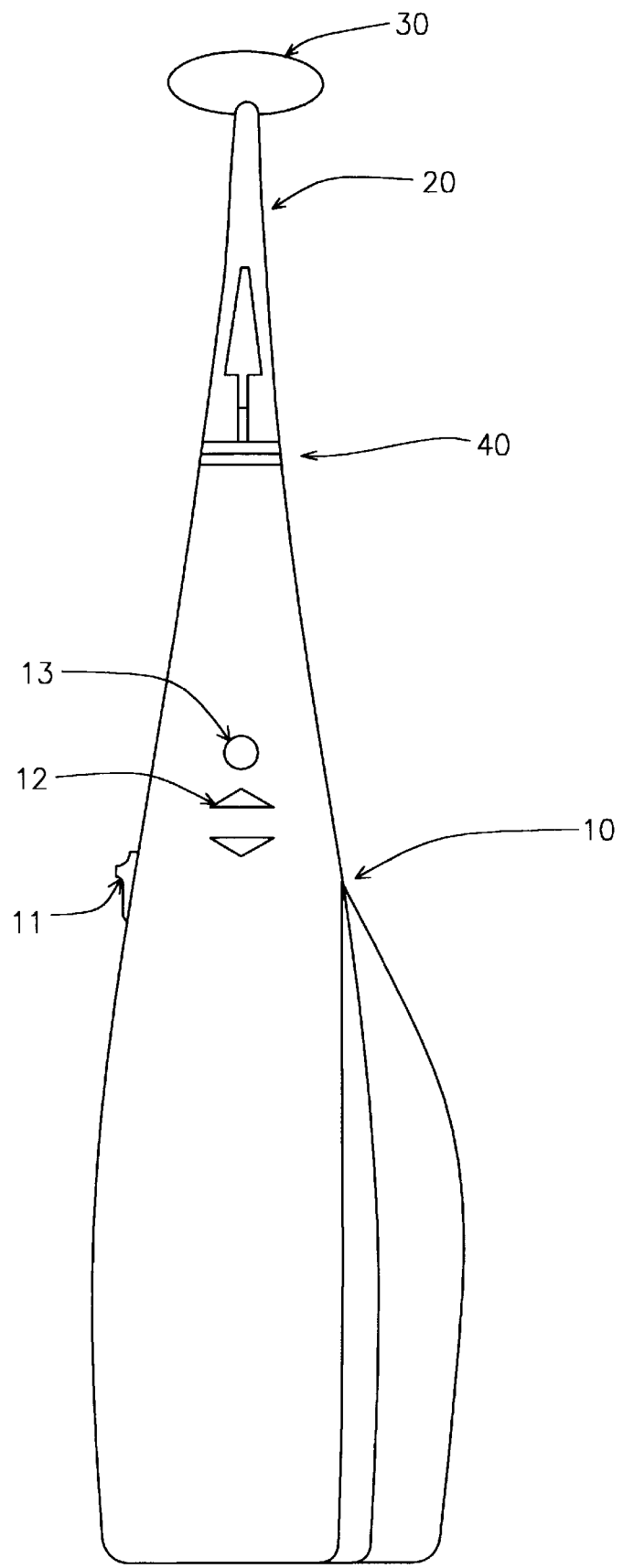
FIG. 1 is a side view of the preferred embodiment.
Figure 4:
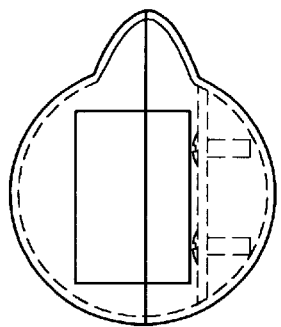
FIG. 4 is a perspective bottom view of the preferred embodiment.

Referring now to FIG. 1, the preferred embodiment of the vibratory apparatus (10) is depicted in a configuration that is ready for use on a patient. The apparatus is light weight and shaped to be easily handled with one single hand. A power switch (11) is placed along the length of the apparatus (10) so that it can be easily manipulated. The frequency of the vibratory force created by the vibratory apparatus can be easily adjusted by the frequency control switches (12). An LED light (13) allows the user to visibly check and adjust the frequency of the vibratory forces. In operation, the user turns on the apparatus (10) with the power switch (11), and then presses either the up or down portion of the frequency control switches (12) until a suitable frequency is indicated by the LED light (13). The extending section (20) is then inserted into the patient's mouth so that the tip (30) rests against the tissue where a shot is to be applied. After the vibratory forces are applied to over-excite the nerves, a shot can be inserted in the area where vibratory forces were applied.

Extending section (20) is firmly connected with the tip (30), and both are preferably composed of a transparent plastic material, although any rigid or semi-rigid material will suffice. Extending section (20) is approximately three inches in length, and made to easily disconnect from the apparatus (10) by a connecting means (40). Extending section (20) can, however, be of any length which allows the apparatus to remain sterile while in use, thus reducing the need for sterilization, because the extending section (20) and tip (30) can be easily replaced after each use. The tip (30) is preferably formed into a smooth and rounded shape that approximates a mathematical oval rotated about its centroid. When made with clear material, the tip allows its user to better see the tissue being treated.

Referring now to FIG. 2, the perspective view of the preferred embodiment shows the solenoid (100) which creates the vibratory force. The solenoid has a plunger (101) which is connected to the extended section (20) by a connecting means (40). The plunger (101) is in an unexcited position when no electrical power is being applied. To achieve this unexcited position, a spring (102) is connected to the plunger (101) and rests against the top of the solenoid (100) so that the spring biases the plunger outwardly to full extension. When power is applied to the solenoid, the plunger (101) moves to an excited position, which is full retraction of the plunger into the solenoid. Preferably, the solenoid has a total movement of approximately 1270 micrometers, thereby simulating a gentle tapping motion which is transmitted to the selected tissue through the extending section and the tip. Preferably, a solenoid having the following specifications is used: a tubular solenoid with a one-half inch diameter and a one inch length, having a flat-faced plunger, a coil wound with 31 AWG magnet wire, a resistance of 9.56 nominal ohms, and 795 turns. In the preferred embodiment, a Lucas solenoid with part number 195202-131 is used, although other similar solenoids can be used instead. This solenoid could create an excessive force and cause damage to the tissue, but the disclosed embodiment only applies the force through the spring (102) to the tissue, thereby avoiding such damage. The solenoid itself is securely fastened to the housing (103) of the apparatus (10) by molded ribs (104).

Figure 7:
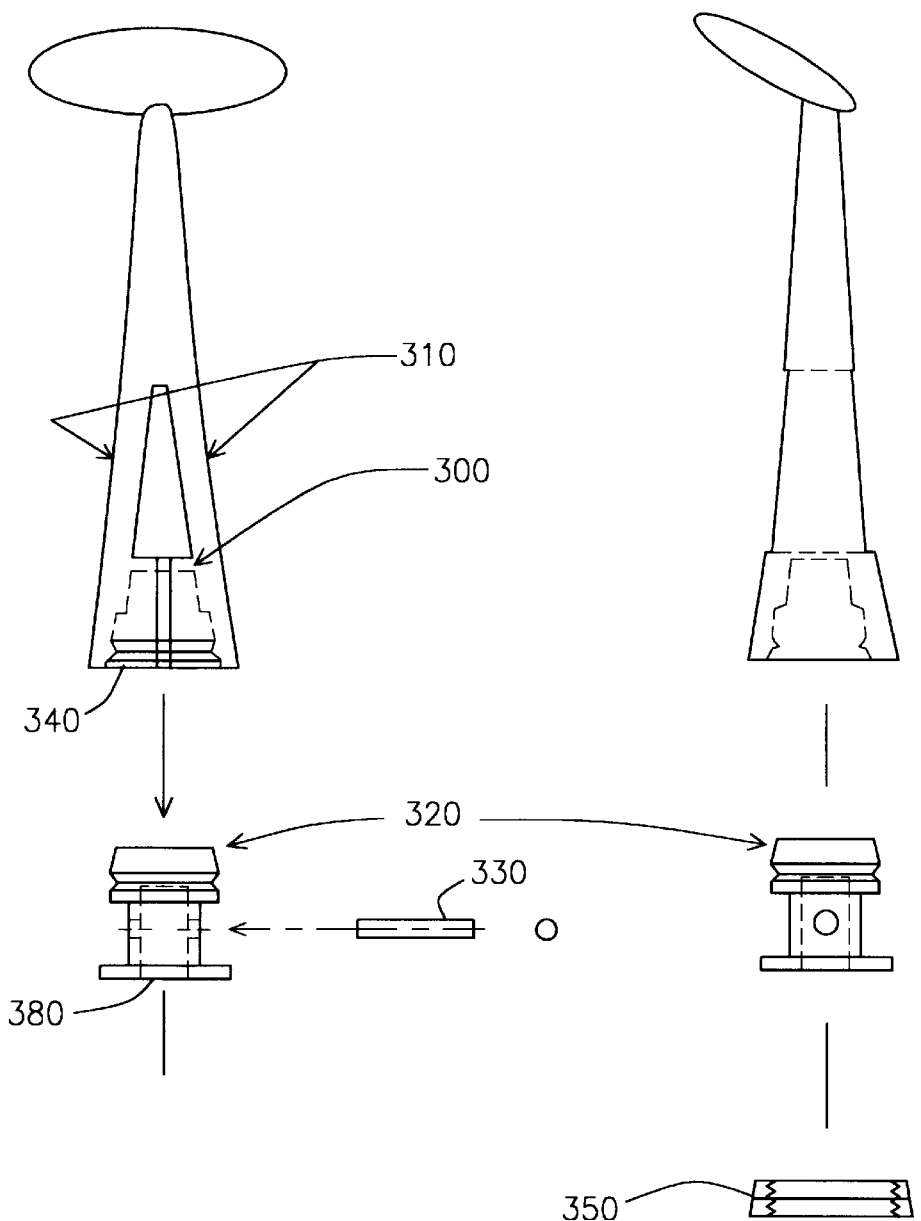
FIG. 7 is a disassembled view of the preferred embodiment of the means for connecting the extending section to the housing of the vibratory apparatus.

Referring now to FIG. 7, the preferred embodiment of the connecting means (40) is shown. The extending section has a living hinge (300) between hollow portions that allows a user to flex the sides of the extending section inward at a pressure point (310). The inward force applied at pressure point (310) forces the collar (340) to flex outward. In this flexed position, the collar (340) easily snaps over the connecting snap piece (320), thereby holding the extending section firmly in place. The connecting snap piece (320) has a slot adapted to accept an anti-rotation pin (330) which has a length greater than the diameter of the connecting snap piece (320). The connecting means (40) is assembled by placing the connecting snap piece (320) into a threaded throat (360) so that the anti-rotation pin (330) fits into a slot (370) formed in the throat (360). The connecting snap piece (320) has a hollow center (380) that is secured over the plunger (101) so that the snap piece follows the motion of the plunger (101) as it alternates between its excited and unexcited positions. A threaded nut (350) is screwed on over the throat (360) to prevent the connecting snap piece from exiting the throat.

Turning back to FIG. 2, power is applied from a battery (140) to a circuit board (130), through an electronic timer (120) and power transistor (110) to the solenoid (100). In the preferred embodiment, the battery is a re-chargeable 7.2 volt Ni-Cad battery. The electronic timer (120) is a common 555 integrated circuit which is connected to the frequency control switches (12). The frequency control switches (12) are preferably a PushPot integrated circuit made by Xicor and sold under part number X9511 which takes input from push buttons and translates that input into digital information and thereby into changes of resistance that controls the output of the 555 circuit. The 555 circuit creates a square wave with a frequency that varies according to the input of the frequency control switches (12), and which is transmitted to a power transistor (110). The power transistor (110) receives this low power signal and in turn supplies a high current to operate the solenoid. Preferably, the transistor is a Darlington type having part number NTE270, although other similar transistors could be used.

Figure 5:
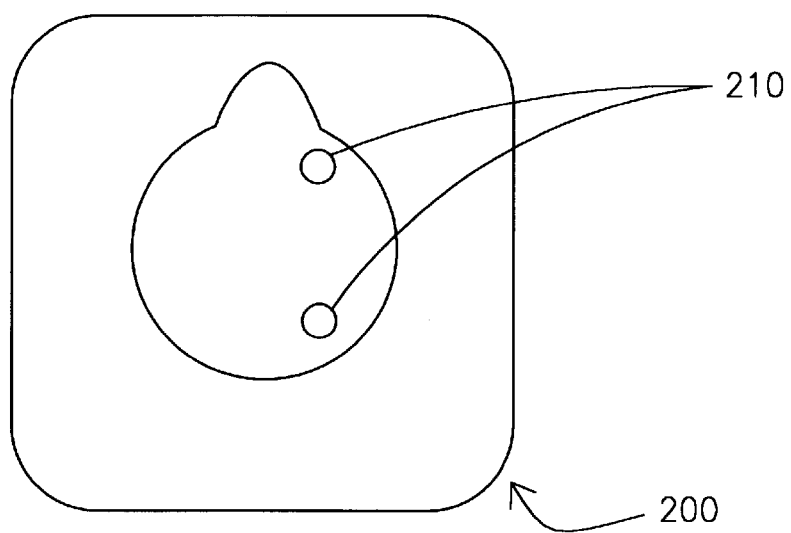
FIG. 5 is a top view of the battery charger stand.
Figure 6:
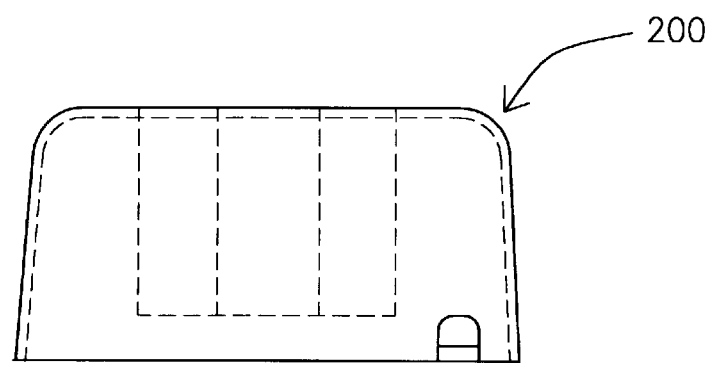
FIG. 6 is a side perspective view of the battery charger stand.

The bottom portion of the housing (103) is adapted to fit in a charging stand (200) depicted in FIG. 5. The charging stand (200) holds the apparatus (10) so that the user can easily reach, remove and apply the apparatus. The housing (103) is formed of two halves which are held together by screws (180) shown in FIG. 3. The screws assembling the halves are placed within the compartment that holds the battery (140). The non-symmetric form of the housing (103) ensures that it will fit in the battery charger stand (200) so that the charging contacts (210) which are depicted in FIG. 5 will only rest against the proper charging posts (220) of the battery.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. For instance, a vibratory force can be created by a number of devices, such as a small electric motor attached to an offcenter weight. It is, therefore, contemplated that the appended claims will cover such modifications that fall within the scope of the invention.

I claim:

1. An apparatus for numbing an area of tissue before inserting a needle containing anesthetic, comprising:

a housing having a top and a bottom, the top having a throat;

a power source;

an electronic timer connected to said power source;

a solenoid located within said housing and connected to said electronic timer, said solenoid having a plunger, said plunger having an excited position and an unexcited position;

an extending section having first and second ends;

connecting means for operationally connecting said extending section to said plunger; and a tip connected to the second end of said extending section, said tip being comprised of a transparent material.

2. An apparatus for numbing an area of tissue before inserting a needle containing anesthetic, comprising:

a housing having a top and a bottom, the top having a throat;

a power source;

an electronic timer connected to said power source;

a solenoid located within said housing and connected to said electronic timer, said solenoid having a plunger, said plunger having an exciting position and an unexcited position;

an extending section having first and second ends;

connected means for operationally connecting said extending section to said plunger, said connected means comprising:

a connecting snap piece operationally connected to said plunger;

a living hinge located in said extending section and having a collar being adapted to snugly fit over said connecting snap piece; and a tip connected to the second end of said extending section.

* * * * *